United States Patent
Haase (10) Patent No.: US 8,100,871 B2
(45) Date of Patent: Jan. 24, 2012

(54) IMPLANTABLE THERAPEUTIC SUBSTANCE DELIVERY SYSTEM WITH CATHETER ACCESS PORT CONTROL AND METHOD OF USE

(75) Inventor: James M. Haase, Maplewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 1449 days.

(21) Appl. No.: 11/413,311

(22) Filed: Apr. 28, 2006

(65) Prior Publication Data

US 2007/0255233 A1 Nov. 1, 2007

(51) Int. Cl.
*A61M 37/00* (2006.01)
(52) U.S. Cl. .................. 604/288.04; 604/288.01
(58) Field of Classification Search ....... 604/288.01–288.04, 131, 890.1–892.1, 604/65–67, 118–121
See application file for complete search history.

(56) References Cited

U.S. PATENT DOCUMENTS

| | | | |
|---|---|---|---|
| 4,482,346 A | 11/1984 | Reinicke | |
| 4,573,994 A | 3/1986 | Fischell et al. | |
| 4,879,553 A | 11/1989 | Righi | |
| 5,169,393 A | 12/1992 | Moorehead et al. | |
| 5,328,465 A | 7/1994 | Kratoska et al. | |
| 5,433,710 A * | 7/1995 | VanAntwerp et al. | 604/152 |
| 5,589,812 A | 12/1996 | Jones | |
| 5,957,890 A | 9/1999 | Mann et al. | |
| 6,114,953 A | 9/2000 | Martin | |
| 6,293,922 B1 | 9/2001 | Haase | |
| 6,520,936 B1 | 2/2003 | Mann | |
| 6,635,049 B1 | 10/2003 | Robinson et al. | |
| 6,663,609 B2 | 12/2003 | Williamson et al. | |
| 6,878,135 B1 | 4/2005 | Haller et al. | |
| 2005/0273082 A1 | 12/2005 | Olsen | |

FOREIGN PATENT DOCUMENTS

| | | |
|---|---|---|
| EP | 0 951 916 A2 | 10/1999 |
| WO | 99/56803 | 11/1999 |
| WO | 01/22185 | 3/2001 |
| WO | 02/17989 | 3/2002 |

OTHER PUBLICATIONS

PCT Search Report mailed Nov. 13, 2007; 13 pgs.

* cited by examiner

*Primary Examiner* — Kevin C Sirmons
*Assistant Examiner* — Phillip Gray
(74) *Attorney, Agent, or Firm* — Dicke, Billig & Czaja, PLLC (57) ABSTRACT

A drug pump including a housing, reservoir, access port, flow restrictor mechanism, and refill port. The housing defines a discharge outlet, and maintains the reservoir in fluid communication with the refill port. The access port is fluidly connected to the discharge outlet. The flow restrictor mechanism is fluidly connected between the discharge outlet and the access port, positioned to establish outflow and inflow directions. The flow restrictor mechanism has flow restriction characteristics in the outflow direction that differ from flow restriction characteristics in the inflow direction. The flow restrictor mechanism partially restricts fluid flow in the outflow direction such that a clinician can sense a difference between an available injection rate through the access port as compared to through the refill port. Further, the flow restrictor mechanism does not overtly impede fluid withdrawal procedures via the access port.

23 Claims, 9 Drawing Sheets

IMPLANTABLE THERAPEUTIC SUBSTANCE DELIVERY SYSTEM WITH CATHETER ACCESS PORT CONTROL AND METHOD OF USE

BACKGROUND OF THE INVENTION

The present invention relates to implantable medical devices for delivering a liquid therapeutic substance to a delivery site within a patient. More particularly, it relates to a system and method for preventing over-infusion through the catheter access port of the delivery device, and related methods of use.

A variety of implantable medical devices are available for treating patients. For example, implantable therapeutic substance delivery devices are typically used to deliver infusion media or therapeutic substances (such as medication) to a patient at a regulated dosage. The implantable therapeutic substance delivery device (sometimes referred to as a drug pump or medicament pump) is implanted by a clinician into a patient at a location appropriate for the therapy. Typically, an infusion catheter is connected to a discharge outlet of the device, and is implanted/positioned to infuse the therapeutic substance at the desired therapy site so as to treat a condition such as pain, spasticity, cancer, neurodegenerative disease, trauma, etc. The term "implantable therapeutic substance delivery device" as used herein, refers to any device for delivering medicaments including, but not limited to, bladder pumps, accumulator pumps, fixed-rate bellows pumps, and the like.

In general terms, the implantable therapeutic substance delivery device commonly includes a drug reservoir containing a volume of the infusion media, along with a pumping mechanism to propel the infusion media in some metered or constant flow dosage to the desired delivery site from the reservoir via the catheter. Over time, the reservoir becomes depleted and it is necessary to refill the device with a new supply of the therapeutic substance. In order to avoid the need for surgery to access and refill the device, it is desirable to have the ability to percutaneously refill the drug reservoir. This is commonly achieved by providing the delivery device with a reservoir refill port that otherwise includes a resilient, resealable septum. The refill port is percutaneously accessible by introducing a hypodermic needle through the skin and into the refill port, and then through the septum, thereby forming a fluid connection between the needle and the drug reservoir. Implantable drug pump devices further commonly include an additional septum port, and in particular a catheter access port. The catheter access port is also accessible percutaneously via hypodermic needle, and provides direct access to the catheter, bypassing the pumping/metering mechanism to allow the infusion of media directly into the patient, or removal of fluid from the patient (e.g., cerebral spinal fluid), via the catheter.

Although many clinicians view the catheter access port as highly desirable, others may be uncomfortable with its presence. In particular, a clinician desiring to refills the reservoir may mistakenly insert the refill needle into the catheter access port instead of the refill port. This can result in a relatively large volume of the drug being administered directly to the patient (i.e., the reservoir and pumping/metering device are bypassed and the refill volume of the drug is directly infused into the patient), potentially resulting in serious problems for the patient. In light of this concern, efforts have been made to enhance the clinician's ability to distinguish the refill port from the catheter access port prior to, or simultaneously with, performing a percutaneous refilling procedure to better ensure that the correct port is accessed. For example, templates have been developed that facilitate the clinician's ability to visualize port locations relative to an exterior of the patient's skin. Further, screens or other needle denial devices can be placed across the catheter access port's opening; this configuration in combination with an appropriately sized refill needle can serve to prevent accidental insertion of the refill needle into the catheter access port. Unfortunately, these techniques may be less than optimal for a particular clinician. Further, if the mis-insertion prevention device(s)/technique(s) are unsuccessful and the refill needle is mistakenly inserted into the catheter access port, once the delivery of infusion media from the needle has begun, the clinician is provided with no additional feedback as to whether the needle has been properly located (or mis-located) within the desired port assembly.

In light of the above, a need exists for a device and method that provides a clinician with feedback information indicative of needle/catheter access port placement during a filling procedure and further that does not overtly impede other desired catheter access port-based procedures.

SUMMARY OF THE INVENTION

Aspects in accordance with principles of the present invention relate to a human implantable liquid therapeutic substance delivery system. The system comprises a delivery device including a housing, a reservoir, an access port assembly, a flow restrictor mechanism, and a refill port assembly. The housing defines a discharge outlet, with the reservoir being maintained by the housing for containing the therapeutic substance. The access port assembly is also associated with the housing and is fluidly connected to the discharge outlet via a fluid pathway. The flow restrictor mechanism is fluidly connected between the discharge outlet and the access port assembly. In particular, the flow restrictor mechanism is positioned so as to establish, relative to the discharge outlet, an outflow fluid flow direction and an inflow fluid flow direction. For example, fluid flow from the flow restrictor mechanism from the discharge outlet is in the outflow direction, whereas fluid flow from the discharge port to the flow restrictor mechanism is in the inflow direction. With this in mind, the flow restrictor mechanism is configured to have flow restriction characteristics in the outflow direction that differ from flow restriction characteristics in the inflow direction. Finally, the refill port assembly is provided apart from the access port assembly and is fluidly connected to the reservoir. With this configuration, the flow restrictor mechanism partially restricts fluid flow from the access port assembly to the discharge outlet such that a clinician can sense a marked difference between the rate of injection allowed by the device when attempting to inject liquid into or through the access port assembly as compared to an available rate of injection into or through the refill port assembly. Further, by providing differing flow restriction characteristics in the inflow direction, the flow restrictor mechanism does not overtly impede a clinician's ability to perform desired liquid exchange (e.g., withdrawal) procedures via the access port assembly. In one embodiment, the system further includes an implantable catheter fluidly connected to the discharge outlet for delivering liquid to and from the desired delivery site within the patient. In a related embodiment, the reservoir and access port assemblies are both fluidly connected to the catheter via the discharge outlet, with the access port assembly thus constituting a catheter access port assembly.

Other aspects in accordance with principles of the present invention relate to a method of percutaneously performing a liquid substance exchange with an implantable therapeutic substance delivery device. The delivery device includes a housing maintaining a reservoir for containing a therapeutic substance, a refill port assembly fluidly connected to the reservoir, and an access port assembly fluidly connected to a discharge port otherwise defined by the housing. With this in mind, the method includes providing a flow restrictor mechanism fluidly connected between the access port assembly and the discharge outlet. In this regard, the flow restrictor mechanism is adapted to partially restrict fluid flow from the access port assembly to the discharge port. Additionally, a liquid delivery system is provided and includes a hypodermic needle fluidly connected to a supply of liquid, with the needle terminating in a needle tip. With this in mind, the needle tip is percutaneously delivered through a septum associated with one of the refill port assembly and the access port assembly. Liquid is initially injected through the needle tip. In connection with this injection, a determination is made as to whether the needle tip is disposed within the refill port assembly or the access port assembly based upon a sensed resistance to fluid flow through the needle tip. Further, based upon this determination, a further determination is made as to whether to move the needle tip to the other port assembly. For example, where the sensed resistance to fluid flow is indicative of a relatively low rate of injection, a determination is made that the needle tip is within the access port assembly. Where the method relates to a reservoir refilling procedure, upon determining that the needle tip is within the access port assembly, the clinician can then decide to discontinue injection of fluid, and move the needle tip to the refill port assembly.

Yet other aspects in accordance with principles of the present invention relate to a human implantable therapeutic substance delivery system including a delivery device. The delivery device includes a housing, a reservoir, an access port assembly, a refill port assembly, and flow restriction means. The housing defines a discharge outlet and maintains the reservoir that otherwise is provided for containing the therapeutic substance. The refill port assembly is also maintained by the housing and is fluidly connected to the reservoir. The access port assembly is provided apart from the refill port assembly and is fluidly connected to the discharge outlet via a fluid pathway. Finally, the flow restriction means is provided for partially restricting a rate of fluid flow across the pathway, at least in a flow direction from the access port assembly to the discharge outlet. Further, the flow restriction means is adapted to permit fluid flow from the discharge outlet to the access port assembly. With this configuration, the flow restriction means provides a user with the ability to sense which of the two port assemblies he/she is interfacing with while performing a percutaneous fluid injection procedure. In one embodiment, the flow restriction means is a self-actuating valve means.

DETAILED DESCRIPTION OF THE INVENTION

Figure 1:
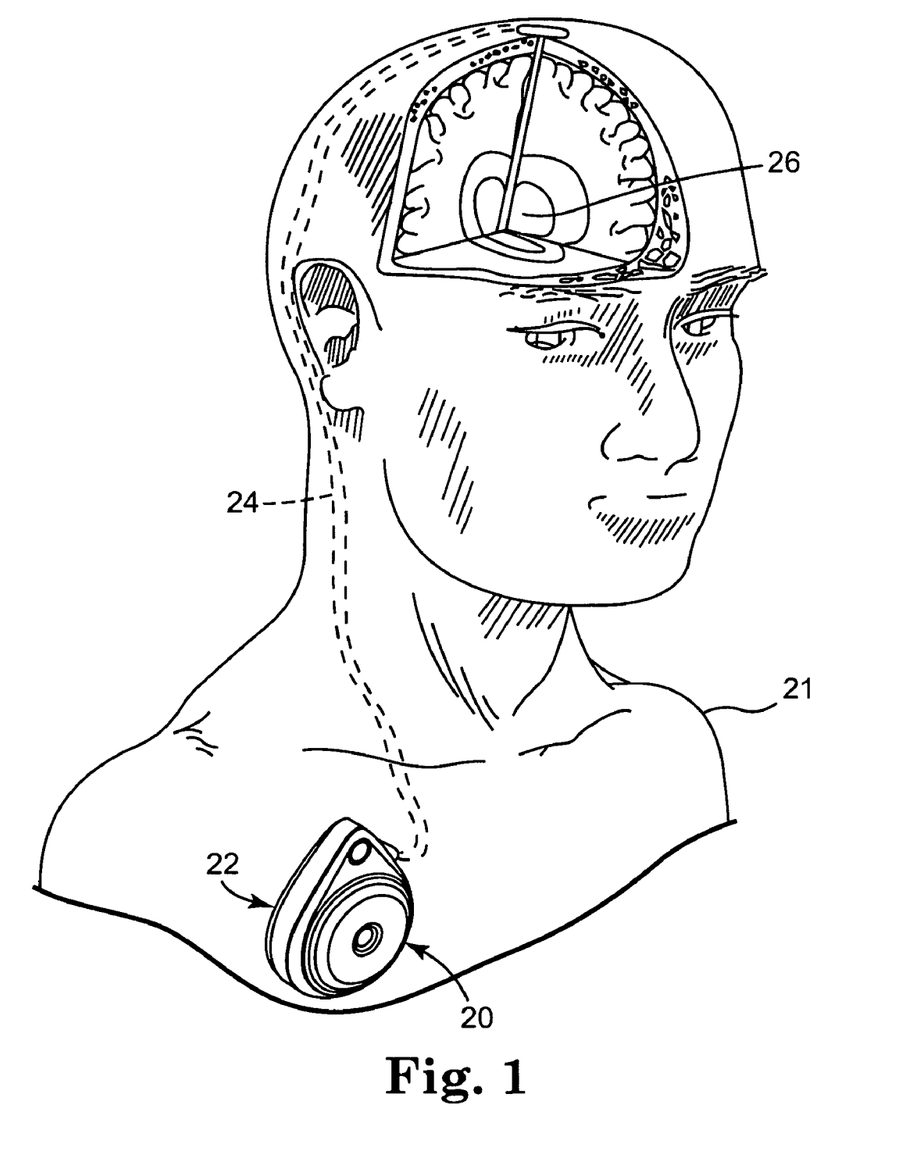
FIG. 1 is a diagrammatic illustration of one human environment in which an implantable therapeutic substance delivery system in accordance with principles of the present invention has been implanted.

FIG. 1 shows one embodiment of an implantable therapeutic substance delivery system 20 in accordance with principles of the present invention, implanted to a patient 21 at but one possible environment for effectuating a treatment. In general terms, and in one embodiment, the system 20 includes an implantable therapeutic substance delivery device 22, also known as a drug pump, and an implantable infusion catheter 24. In other embodiments, the system 20 can further include a remote programmer (not shown) for interfacing with the delivery device 22 from a point outside of the patient 21. Regardless, the therapeutic substance delivery device 22 can be used for a wide variety of therapies to medical conditions (also known as medical indications) such as pain, spasticity, cancer, and many other medical conditions. The delivery device 22 is typically implanted by a clinician in a sterile surgical procedure performed under a local, regional, or general anesthesia. Before implanting the delivery device 22, the catheter 24 is typically implanted with the distal end thereof positioned at the desired therapeutic substance infusion site and a proximal end tunneled to the location where the delivery device 22 is to be implanted. In alternative embodiments, the delivery device 22 is configured to delivery therapeutic substance directly to the patient 21, such that the catheter 24 can be eliminated. Regardless, the delivery device 22 is generally implanted subcutaneously beneath the skin where there is sufficient subcutaneous tissue to support the device 22. Once implanted, the delivery device 22 operates to infuse a therapeutic substance (not shown) at a desired rate into the patient. As is known in the art, the therapeutic substance is a product or substance intended to have a therapeutic effect, such as pharmaceutical compositions, genetic materials, biologics, and other substances. Other substances are intended to have a therapeutic effect yet are not easily classified such as saline solution, fluoroscopy agents, and the like.

Figure 2A:
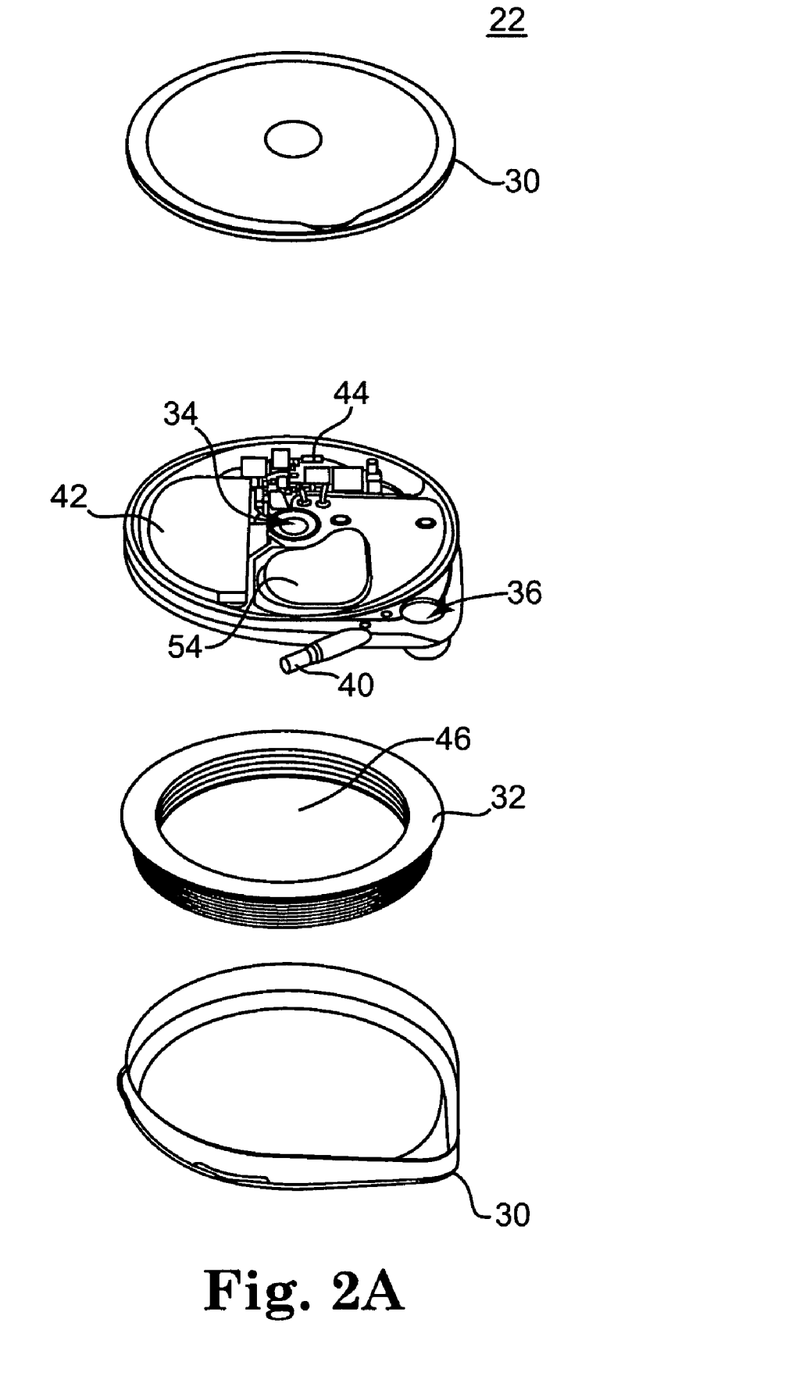
FIG. 2A is an exploded view of one embodiment implantable therapeutic substance delivery device in accordance with principles of the present invention.
Figure 2B:
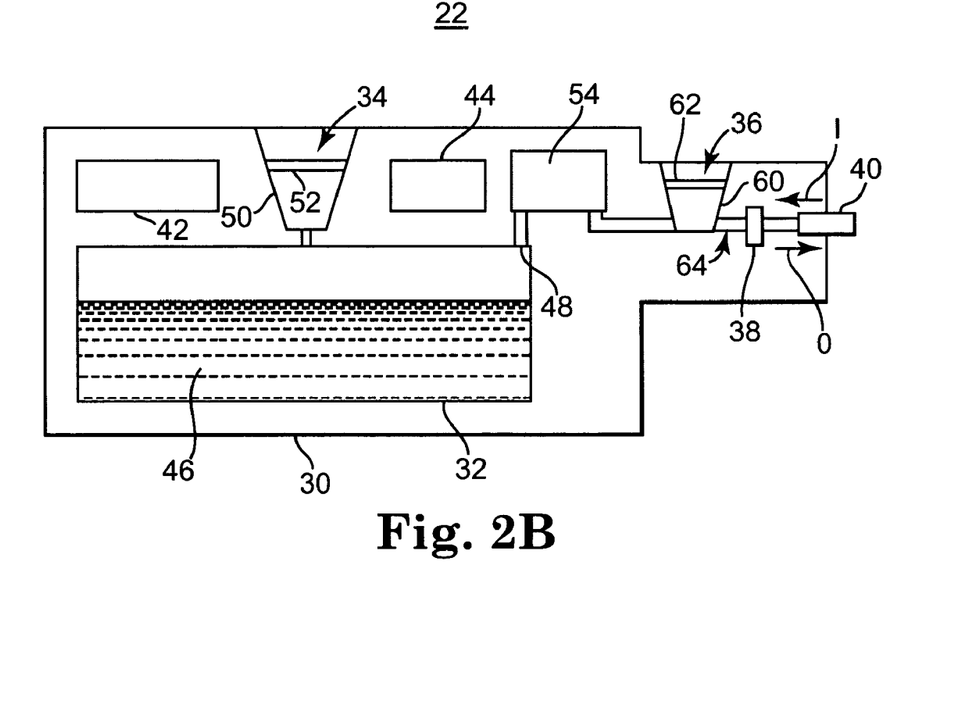
FIG. 2B is a schematic illustration of the device of FIG. 2A, with portions shown in block form.

With the above in mind, FIGS. 2A and 2B show an exploded view and schematic illustration, respectively, of one embodiment of the delivery device 22 in accordance with principles of the present invention. In particular, in one embodiment, the delivery device 22 includes a housing 30, a reservoir 32, a refill port assembly 34, an access port assembly 36, and a flow restriction means such as a flow restrictor mechanism 38 (hidden in the view of FIG. 2A; illustrated in block form in FIG. 2B). The housing 30 maintains and/or forms the various components 32-38 and further forms or maintains a discharge outlet 40. In some embodiments, the discharge outlet 40 is configured to be fluidly coupled to the catheter 24 (FIG. 1) as previously described. Apart from the flow restrictor mechanism 38, the delivery device 22 can be akin to conventional drug pump configurations such as the SynchroMed® EL infusion system or the IsoMed™ constant flow infusion system, both available from Medtronic, Inc., of Minneapolis, Minn.; the Paradigm® insulin pump available from Medtronic-MiniMed, Inc., of Northridge, Calif.; etc.; and thus can, in some embodiments, include additional components such as, for example, a power source 42, electronics 44, etc. Unlike these and other conventional designs, however, the flow restrictor mechanism 38 serves to partially restrict fluid flow from the access port assembly 36 to the discharge outlet 40 as described in greater detail below.

In terms of general construction, the reservoir 32 is maintained by the housing 30 and is adapted for containing the liquid therapeutic substance 46 (illustrated generally in FIGS. 2A and 2B). The reservoir 32 forms a reservoir outlet 48 (FIG. 2B) through which the contained therapeutic substance 46 is dispensed. Further, the reservoir 32 is fluidly connected to the refill port assembly 34 that otherwise facilitates filling of the reservoir 32 from a point exterior the housing 30. As shown in FIG. 2B, the refill port assembly 34 is of a type known in the art and generally includes a passage wall 50 across which a septum 52 is disposed.

The reservoir 32 can include or form a variety of structures or mechanisms useful to facilitate continuous, positive availability of the therapeutic substance 46 at the reservoir outlet 48, such as bellows acted upon by a propellant as is known in the art. Further, in some embodiments, a pumping and/or metering mechanism 54 as is known in the art (collectively or individually referred to herein as a "metering mechanism") can be provided to assist in directing or controlling flow of the therapeutic substance 46 from the reservoir outlet 48. In the one embodiment shown in FIG. 2B, the metering mechanism 54 fluidly connects the reservoir 32 with the discharge outlet 40, such that the therapeutic substance 46 from the reservoir 32 is dispensed from the delivery device 22 via the discharge outlet 40. In alternative embodiments described below, however, the reservoir outlet 48 can be fluidly connected to a separate or second discharge outlet that is not otherwise fluidly connected to the discharge outlet 40 (and thus the access port assembly 36).

Similar to the refill port assembly 34, the access port assembly 36 includes a passage wall 60 across which a septum 62 is disposed. The access port assembly 36 can assume a variety of forms known in the art, and can, in some embodiments, include additional features such as a screen (not shown) adapted to limit a size of a hypodermic needle (not shown) that can otherwise interface with the septum 62. Regardless, the access port assembly 36 is fluidly connected to the discharge outlet 40 via fluid pathway 64. Further, the flow restrictor mechanism 38 is fluidly coupled within the fluid pathway 64, between the access port assembly 36 and the discharge outlet 40. Thus, fluid flow between the access port assembly 36 and the discharge outlet 40 must pass through the flow restrictor mechanism 38, with the flow restrictor mechanism 38 affecting this flow as described below. As a point of reference, a flow direction through the flow restrictor mechanism 38 can be described relative to the discharge outlet 40 and/or the access port assembly 36. In particular, an inflow direction (the arrow "I" in FIG. 2B) represents fluid flowing from the discharge outlet 40 to the access port assembly 36, whereas an outflow direction (the arrow "O" in FIG. 2B) refers to fluid flowing from the access port assembly 36 to the discharge outlet 40.

Figure 3:
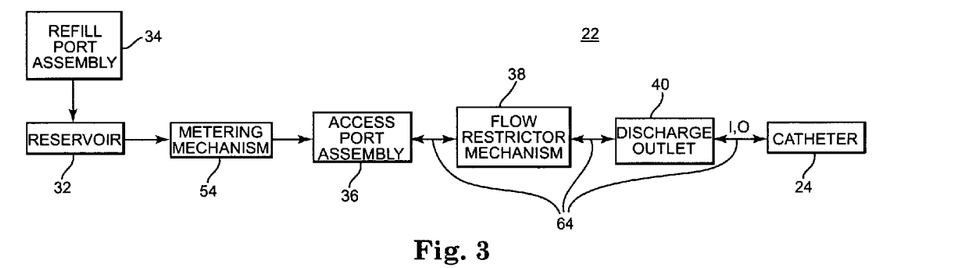
FIG. 3 is a block diagram of the device of FIG. 2A, illustrating a fluid pathway.

FIG. 3 illustrates fluid pathway(s), including the fluid pathway 64, established by the delivery device 22 in accordance with some embodiments of the present invention. In particular, the refill port assembly 34 provides a fluid connection to the reservoir 32. Thus, the refill port assembly 34 facilitates filling (or re-filling) of the reservoir 32 with the therapeutic substance 46 (FIG. 2B). The therapeutic substance 46 is delivered from the reservoir 32 to the metering mechanism 54. With the one embodiment of FIG. 3, the metering mechanism 54 is fluidly connected to the discharge outlet 40, and thus the catheter 24, along the fluid pathway 64. The access port assembly 36 is also fluidly connected along the fluid pathway 64, between the metering mechanism 54 and the discharge outlet 40. With this one embodiment, then, the refill port assembly 34 and the access port assembly 36 are fluidly arranged in series relative to the discharge outlet 40. In one embodiment, the metering mechanism 54 is configured to prevent the flow of fluid from the access port assembly 36 back through the metering mechanism 54 and to the reservoir 32. Alternatively, a one-way valve (not shown) can be fluidly coupled between the access port assembly 36 and the metering mechanism 54. Regardless, the flow restrictor mechanism 38 is fluidly coupled between the access port assembly 36 and the discharge outlet 40. As shown by arrowheads in FIG. 3, fluid flow can occur in two directions (i.e., the inflow direction I and the outflow direction O) relative to the access port assembly 36, the flow restrictor mechanism 38, and the discharge outlet 40. With this configuration, then, a desired liquid can be introduced to the discharge outlet 40 (and thus to the catheter 24 where provided) via the access port assembly 36, and can be withdrawn from the discharge outlet 40 (and thus from the catheter 24 where provided) via the access port assembly 36. In this regard, the flow restrictor mechanism 38 is adapted such that the flow rate characteristics associated with the injection of liquid through the access port assembly 36 (outflow direction O) differs from the flow rate characteristics associated with withdrawal of liquid through the access port assembly 36 (inflow direction I).

Figure 4A:
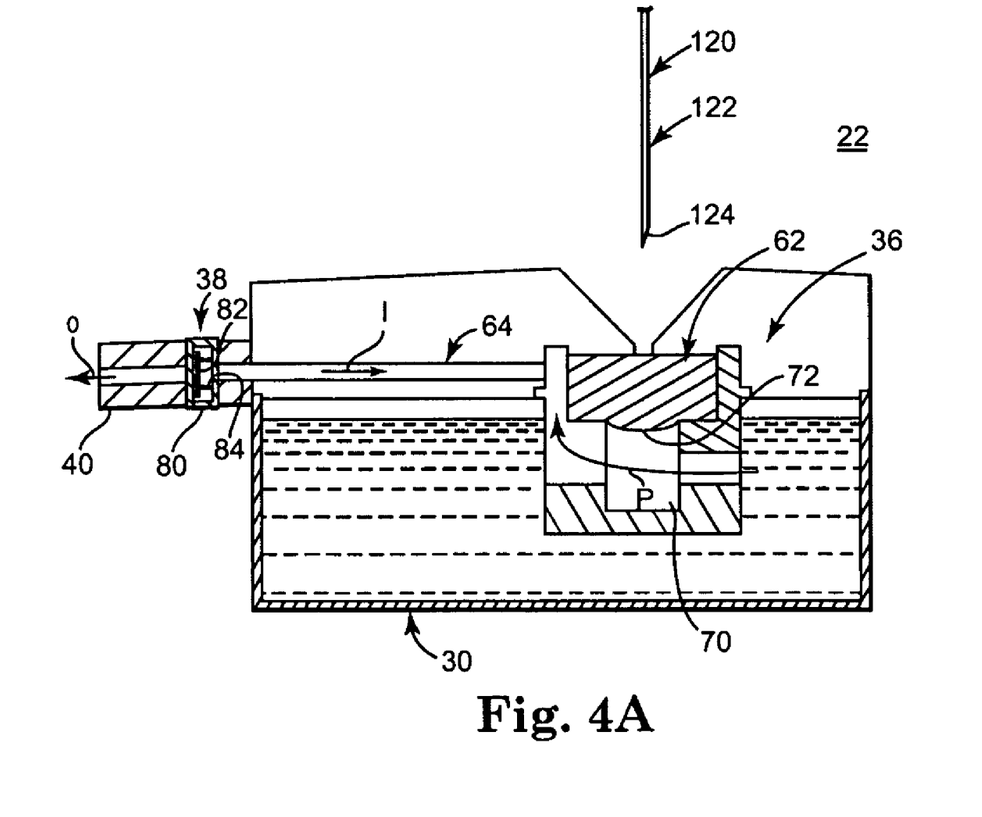
FIG. 4A is a simplified cross-sectional view of the device of FIG. 2A illustrating an access port assembly and flow restrictor mechanism in accordance with principles of the present invention.

In particular, and with the one embodiment of FIG. 4A, the flow restrictor mechanism 38 is configured to restrict or limit fluid flow in the outflow direction O to a greater extent than in the inflow direction I. As a point of reference, with the one embodiment of FIG. 4A, the access port assembly 36 is shown as including a well 70 adjacent an inner face 72 of the access port assembly septum 62. The well 70, in turn, is fluidly connected to the fluid pathway 64 that otherwise communicates fluids (i.e., the therapeutic substance 46 (FIG. 2B)) from the metering mechanism 54 (hidden in the view of FIG. 4A) to the discharge outlet 40 (with this flow being generally represented by the arrow "P" in FIG. 4A)). With this in mind, in one embodiment the flow restrictor mechanism 38 is akin to a check valve and includes a cylinder 80, a valve plate 82, and a biasing device 84. The flow restrictor mechanism 38 is shown in greater detail in FIG. 4B. The cylinder 80 slidably maintains the valve plate 82, with the biasing device 84 biasing the valve plate 82 to a desired position or location within the cylinder 80 as described below.

Figure 4B:
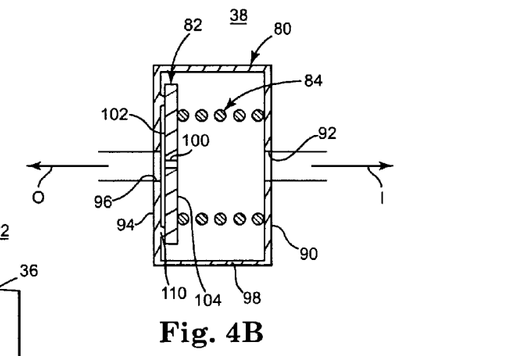
FIG. 4B is an enlarged, cross-sectional view of the flow restrictor mechanism of FIG. 4A.

The cylinder 80 can assume a variety of forms, and is generally sized for assembly along the discharge outlet 40. Alternatively, the flow restrictor mechanism 38 can be configured for assembly at other locations relative to the housing 30. Regardless, the cylinder 80 defines an inlet face 90 forming an inlet opening 92, and an outlet face 94 defining an outlet opening 96. The openings 92, 96 can assume a variety of diameters, but are, in one embodiment, preferably the same or greater than a diameter associated with the fluid pathway 64 immediately upstream of the flow restrictor mechanism 38. Finally, the inlet and outlet faces 90, 94 are formed at opposite ends of a side wall 98 otherwise defining an inner diameter of the cylinder 80.

The valve plate 82 is disposed within the cylinder 80, and forms at least one orifice 100, a first face 102, and an opposing second face 104. In one embodiment, an outer diameter of the valve plate 82 is greater than a diameter of the openings 92, 96, such that the valve plate 82 can nest against, or relative to, one or both of the inlet or outlet faces 90, 94 when so-positioned. However, an outer diameter of the valve plate 82 is selected to be less than an inner diameter of the cylinder 80 such that the valve plate 82 can readily slide back and forth within the cylinder 80 (represented by an arrow in FIG. 4B); further, a sufficient spacing exists between a perimeter of the valve plate 82 and the cylinder side wall 98 such that fluid flow can readily occur between the cylinder side wall 98 and an outer perimeter of the valve plate 82. More particularly, a total open area defined between the valve plate 82 perimeter and the cylinder side wall 98 is not less than approximately the cross-sectional area defined by other of the openings 92, 96 such that when the valve plate 82 is in an opened position or state (described below), the combination valve plate 82/cylinder side wall 98 does not present a substantial restriction to fluid flow between the openings 92, 96. The valve plate 82 can be formed from a variety of materials compatible with the therapeutic substance 46 (FIG. 2B) to be dispensed, capable of providing a fluid tight seal relative to other component(s) of the flow restrictor mechanism 38 (as described below), and in some embodiments can be a membrane.

The orifice 100 is, in one embodiment, centered relative to a perimeter of the valve plate 82. In other embodiments, the orifice 100 is off-set from the valve plate 82 center point. Regardless, the orifice 100 extends through a thickness of the valve plate 82 and has, in one embodiment, a diameter smaller than that of either of the inlet or outlet openings 92, 96. Thus, when the valve plate 82 is sealed against, or relative to, the outlet face 94, fluid flow through the flow restrictor mechanism 38 is limited by the orifice 100. To this end, the outlet face 94 can further form a flange 110 against which the valve plate 82 can abut in a sealed relationship. Alternatively and/or in addition, a gasket or similar body can be provided to effectuate a desired seal. Regardless, in one embodiment, the orifice 100 has a diameter in the range of 0.0005-0.05 inch; more preferably in the range of 0.001-0.1 inch; even more preferably approximately 0.005 inch (plus or minus 0.001 inch). As described below, it has surprisingly been discovered that by forming the orifice 100 to have a diameter of approximately 0.005 inch, the flow restrictor mechanism 38 will exhibit desired flow characteristics enabling a clinician to consistently sense that fluid is being injected through the access port assembly 36, while still facilitating desired fluid withdrawal procedures as described below. While the valve plate 82 has been described as providing the one orifice 100, in other embodiments, a plurality of orifices can be formed, with a combined opening size or area of the orifices preferably conforming with the dimensional attributes listed above.

Finally, the biasing device 84 is configured to bias the valve plate 82 to the position of FIGS. 4A and 4B in which the valve plate 82 is seated against or relative to the outlet face 94 of the cylinder 80. In one embodiment, the biasing device 84 is a helical spring, although other biasing configurations are also acceptable. Preferably, however, the biasing device 84 does not overtly impede fluid flow through the cylinder 80 (apart from acting upon the valve plate 82), and imparts a predetermined force onto the second face 104 of the valve plate 82 at a level that can be overcome in the presence of a vacuum applied to the second face 104. For example, in accordance with the one embodiment in which the biasing device 84 is a spring, the spring 84 can have a spring force selected such that a force imparted by the spring 84 onto the valve plate 82 can be overcome (i.e., the valve plate 82 moves toward the inlet face 90) when a vacuum on the order of 5 psi (plus or minus 2 psi) is formed within the cylinder 80 at the second face 104 of the valve plate 82. Under these conditions, the spring force of the biasing device 84 is overcome such that the valve plate 82 will move toward the inlet face 90 (i.e., rightward relative to the orientation of FIGS. 4A and 4B). This, in turn, results in the valve plate 82 no longer being sealed relative to the outlet face 94, such that the orifice 100 no longer serves as the sole conduit through which fluid can move through the flow restrictor mechanism 38. By way of example, the desired vacuum pressure can readily be created by a clinician operating a standard hypodermic needle assembly to otherwise create a vacuum within the access port assembly 36 (FIG. 4A) that, in turn, is applied to the flow restrictor mechanism 38 as described. Regardless, once the vacuum is reduced or eliminated, the biasing device 84 acts to force the valve plate 82 back into a sealed relationship with the outlet face 94. Thus, in one embodiment, the flow restrictor mechanism 38 is a self-actuating valve.

During use, the delivery device 22 operates in a manner highly similar to known implantable drug pumps, with the metering mechanism 54 (FIG. 2B) delivering the therapeutic substance 46 (FIG. 2B) from the reservoir 32 (FIG. 2B) to the discharge outlet 40, and thus the catheter 24, via the fluid pathway 64. As a point of reference, with the one embodiment of FIG. 4A, the flow restrictor mechanism 38 is fluidly in series between the metering mechanism 54 and the discharge outlet 40. Thus, the flow of therapeutic substance 46 from the metering mechanism 54 passes through the flow restrictor mechanism 38. However, in one embodiment, the flow restrictor mechanism 38 is configured so as to not overtly restrict fluid flow from the metering mechanism 54 to the discharge outlet 40 at the flow rates normally employed with implantable drug delivery devices. For example, conventional implantable therapeutic substance delivery devices are adapted to provide a maximum bolus rate of 24 mL per day, with the normal bolus delivery rate being on the order of 0.1-1.0 mL per day. With this in mind, with the one embodiment in which the flow restrictor mechanism 38 includes the valve plate 32 having the orifice 100, by forming the orifice 100 to have a diameter of approximately or on the order of 0.005 inch, the normal bolus delivery rate is not affected. That is to say, in the sealed position of FIG. 4A, the flow restrictor mechanism 38 allows for continuous flow of the therapeutic substance 46 from the metering mechanism 54 to the discharge outlet 40 over the entire range of normal bolus delivery rates. As described below, in alternative embodiments, the delivery device 22 can alternatively be configured to establish a fluid pathway from the metering mechanism 54 that is branched from the flow restrictor mechanism 38.

Figure 4C:
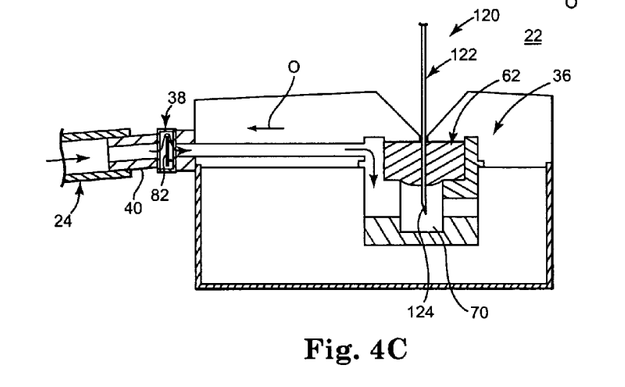
FIG. 4C is a simplified cross-sectional view of the device of FIG. 4A in an open or unsealed state.

In addition to facilitating normal operation of the delivery device 22 in terms of delivering the therapeutic substance 46 (FIG. 2B) to the patient, the delivery device 22 further permits procedures normally performed through the access port assembly 36. For example, a percutaneous fluid withdrawal procedure can be performed using a hypodermic needle assembly 120 (referenced generally in FIG. 4A) that includes a needle 122 having a needle tip 124 as shown. In particular, the needle tip 124 is directed to the access port assembly 36 and pierced through the septum 62. Once the needle tip 124 is positioned within the well 70, a vacuum is applied to the well 70 via the needle 122 (e.g., by the clinician retracting a plunger (not shown) provided with the hypodermic needle assembly 120 as is conventionally known). The vacuum, in turn, is applied to the second face 104 (FIG. 4B) of the valve plate 82. Once the vacuum exceeds a certain level (e.g., approximately 5 psi), the force imparted by the biasing device 84 onto the valve plate 82 is overcome, with the vacuum further causing the valve plate 82 to move from the sealed or closed state or position of FIG. 4A to an unsealed or open state or position illustrated in FIG. 4C. In the unsealed state or position, the vacuum pressure is further imparted through the discharge outlet 40 and, where provided, the catheter 24, causing liquid at the patient site (not shown) to enter the catheter 24/discharge outlet 40. As shown by arrows in FIG. 4C, the liquid being withdrawn (e.g., bodily fluids such as cerebral spinal fluid) flows through and around the valve plate 82 and back to the access port assembly 36 where it is then withdrawn through the needle tip 124. Thus, the flow restrictor mechanism 38 in accordance with some embodiments of the present invention allows for unobstructed withdrawal of fluid out of the catheter 24 and into the access port assembly 36, thus satisfying a desire for quick and easy fluid withdrawal.

In addition, the flow restrictor mechanism 38 allows for the injection of liquid through the access port assembly 36 and to the discharge outlet 40 (and thus to the catheter 24 where provided). In this regard, typical injection procedures performed through the access port assembly 36 entail determining or diagnosing whether the catheter 24 is blocked. To perform a blocked catheter diagnosis procedure, typical procedures require the injection of a minimal amount of liquid (on the order of 1 cc) in order to fill the catheter 24 and thus locate a potential obstruction within the catheter 24. With this in mind the needle tip 124 is again located within the access port assembly 36 and pierced through the septum 62. Once the needle tip 124 is within the well 70, injection of liquid through the needle tip 124 can occur. The injected liquid flows in the outflow direction O. As a result, the valve plate 82 is in the sealed state or position of FIG. 4A, necessitating that the injected liquid must pass through the orifice 100. Thus, although the flow restrictor mechanism 38 places a restriction onto liquid flow from the access port assembly 36, due to the relatively small volume of liquid being injected as part of a blocked catheter diagnosis procedure, the time required to complete the injected procedure is relatively minimal. For example, in accordance with one embodiment in which the orifice 100 (FIG. 4B) of the valve plate 82 has a diameter of approximately 0.005 inch, 1 cc of liquid can pass through the flow restrictor mechanism 38 in less than one minute, such that a blocked catheter diagnosis procedure can readily be performed.

In addition to facilitating performance of all desired procedures normally associated with an implantable therapeutic substance delivery device, the delivery device 22 of the present invention provides the clinician with the ability to tactilely recognize the port assembly 34 (FIG. 2B) or 36 within which the needle tip 124 is placed during an injection procedure. As a point of reference, conventional drug pump refill assemblies (that otherwise include the hypodermic needle assembly 120 shown in FIG. 4A having the needle 122/needle tip 124) are capable of delivering a relatively large volume of liquid (on the order of 20 mL) in a relatively short time frame (e.g., 30-60 seconds). Relative to the reservoir 32 (FIG. 2B), the refill port assembly 34/reservoir 32 present no flow restrictions onto fluid being delivered from the needle tip 124 to the reservoir 32 (apart from the reservoir 32 being full). Thus, for example, the clinician can expect to complete a refill procedure in which 20 mL of the therapeutic substance 46 is delivered or filled into the reservoir 32 in 30-60 seconds. In the absence of the flow restrictor mechanism 38, a similar flow rate would also be achieved were the injection to be performed through the access port assembly 36. However, the flow restrictor mechanism 38 overtly limits fluid flow in the outflow direction O. In particular, and again by way of non-limiting example, where the flow restrictor mechanisms 38 has the configuration shown in FIGS. 4A and 4B, including the valve plate 82 with the orifice 100 having a diameter of approximately 0.005 inch, the maximum flow rate achieved through the flow restrictor mechanism 38, and thus from the access port assembly 36 to the discharge outlet 40, is such that a clinician attempting to dispense 20 mL of liquid through the conventional hypodermic needle 122 will require a delivery time on the order of 5 minutes. Thus, where a clinician, otherwise desiring to perform a reservoir refill procedure, accidentally locates the needle tip 124 within the access port assembly 36 and then begins to inject the therapeutic substance 46 through the needle 122, the clinician will tactilely (or otherwise) notice a marked resistance to fluid flow through the needle 122 as compared to the flow rate expected when interfacing with the refill port assembly 34. This, in turn, provides the clinician with the ability to quickly evaluate whether the refill procedure is being performed through the proper port assembly (i.e., the refill port assembly 34).

In light of the above, the flow restrictor mechanism 38 is configured such that a maximum flow rate from the access port assembly 36 to the discharge outlet 40 is less than a maximum flow rate from the refill port assembly 34 to the reservoir 32; more preferably at least two times less; even more preferably at least three times less; and even more preferably at least four times less. Further, the flow restrictor mechanism 38 is configured such that a maximum available flow rate from the discharge outlet 40 to the access port assembly 36 (inflow direction I) is greater than a maximum available flow rate from the access port assembly 36 to the discharge outlet 40 (outflow direction O); more preferably at least two times greater; and even more preferably at least three times greater.

Figure 5:
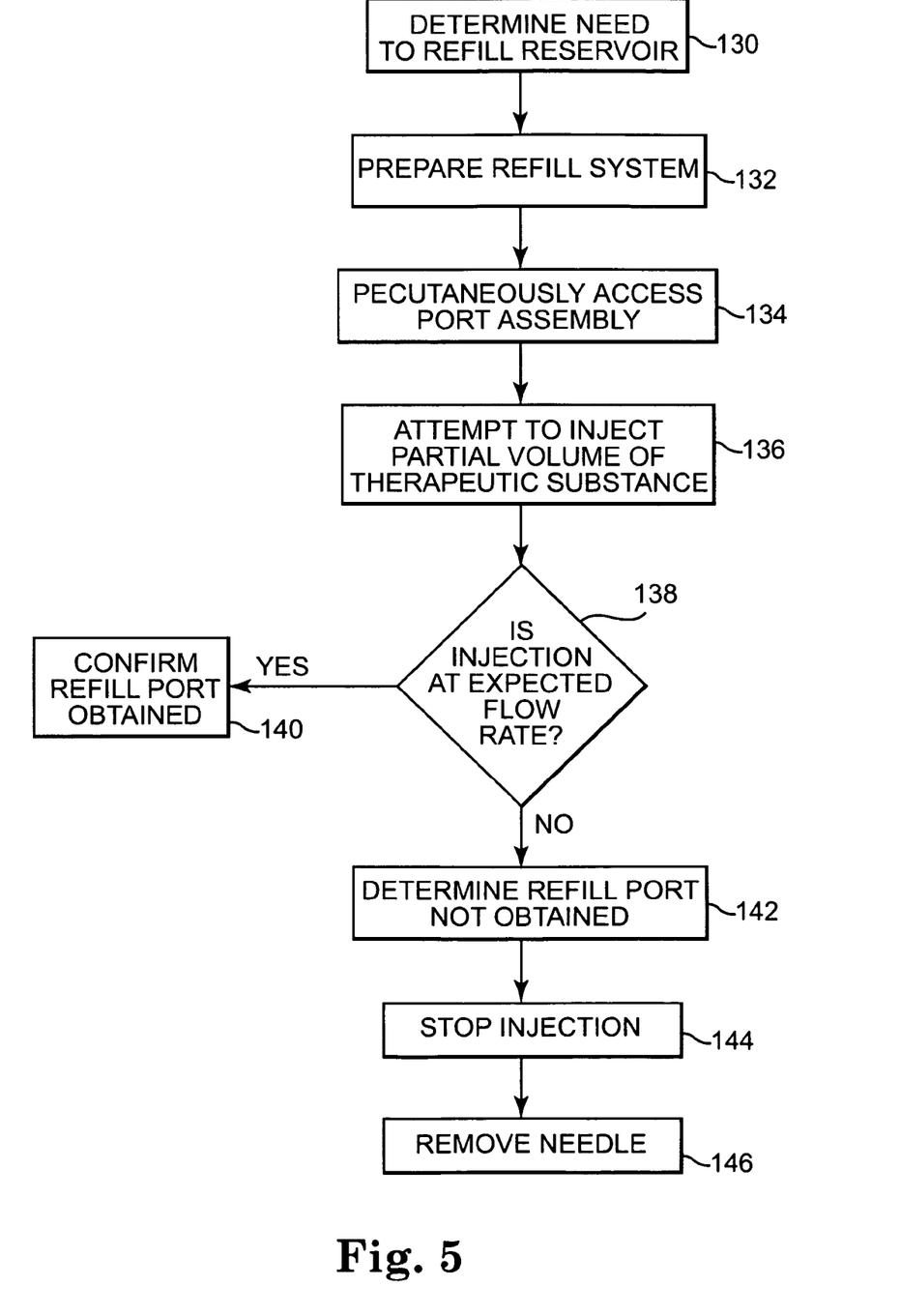
FIG. 5 is a flow diagram relating to one method of percutaneously exchanging liquid with an implantable therapeutic substance delivery device in accordance with principles of the present invention.

The flow diagram of FIG. 5 illustrates one exemplary embodiment of a percutaneous liquid exchange procedure in accordance with aspects of the present invention. More particularly, a method of refilling the reservoir 32 is described, it being understood that systems and methods in accordance with the present invention include other percutaneous liquid exchange procedures, such as a desired infusion of liquid substance through the access port assembly 36 to the discharge outlet 40, as well as withdrawal of fluid from or through the discharge outlet 40 to the access port assembly 36 as previously described. With additional reference to FIGS. 4A and 4B, following implantation of the delivery device 22, the clinician determines that the reservoir 32 associated therewith needs to be refilled with the therapeutic substance 46 at step 130. At step 132, the clinician prepares the therapeutic substance refilling or liquid supply system (e.g., a hypodermic needle/syringe assembly) that otherwise includes the needle 122 having the needle tip 124. Once prepared, the needle tip 124 percutaneously accesses one of the port assemblies 34, 36 at step 134. In this regard, efforts can be made by the clinician to initially determine the locations of the refill port assembly 34 and the access port assembly 36 (e.g., palpating a periphery of the pump device 22 and/or one or both of the port assemblies 34, 36 through the patient's skin, use of a template, etc.) so that initial insertion of the needle tip 124 properly occurs to and through the refill port assembly 34 as opposed to the access port assembly 36. As previously indicated, however, it is at times difficult to know with certainty that the refill port assembly 34 has been obtained.

Once the clinician has decided that the needle tip 124 has pierced through the septum 52 or 62 associated with the port assembly 34 or 36 within which the needle tip 124 is actually placed, at step 136, the clinician attempts to inject a partial volume of the therapeutic substance 46 through the needle 122. In connection with this initial injection, at step 138, the clinician evaluates or senses whether the rate at which the therapeutic substance 46 is being dispensed through the needle tip 124 is slower than expected. For example, based on past experience and/or specified refilling guidelines provided with the delivery device 22 and/or the refilling system, the clinician estimates or observes whether the entire volume of the therapeutic substance 46 intended to be delivered can be completely delivered within normally expected timeframes, or conversely whether, at the current rate of injection being experienced, complete injection will take several or more minutes (e.g., otherwise indicative of a longer than expected refilling time). Alternatively and/or in addition, the refilling system can be configured to provide the clinician with information indicative of a current rate of dispensement (or flow rate) from the needle tip 124, with the clinician comparing this rate with flow rate guidelines to determine whether the current rate of injection is slower than expected. In other embodiments, where the refilling system includes a conventional cylinder/plunger arrangement, the clinician can tactilely "feel" whether the resistance to a clinician-generated force placed upon the plunger is greater than expected. Any or all of these feedback observations are indicative of fluid flow occurring from the needle tip 124 to the flow restrictor mechanism 38 (as opposed to the reservoir 32 as otherwise intended).

If the clinician determines that the injection rate is comparable with the expected rate, it can be confirmed at step 140 that the needle tip 124 is properly located within the refill port assembly 34, and thus that the therapeutic substance 46 is being delivered to the reservoir 32.

Conversely, if it is determined at step 138 that the injection rate being achieved is much slower than expected, the clinician can determine at step 142 that the needle tip 124 has accidentally been incorrectly placed within the access port assembly 36. Based upon this determination, at step 144, the clinician can then decided to cease the injection procedure, followed by removal of the needle tip 124 from the port assembly 36 (or 34) at step 146. The method then returns to step 134 at which the clinician again attempts to percutaneously deliver the needle tip 124 to the refill port assembly 34.

Figure 6A:
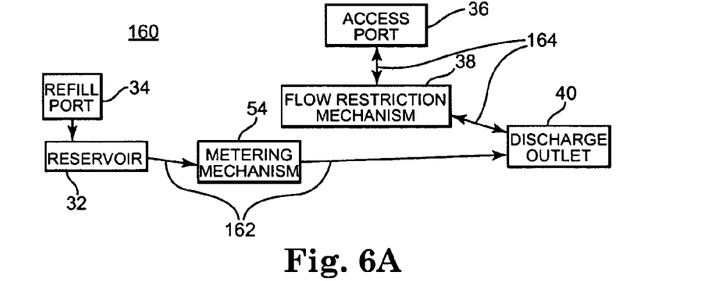
FIGS. 6A-6C are block diagrams of fluid pathways in accordance with alterative embodiments of the present invention.

Although the delivery device 22, and related method of use, have been described in the context of the access port assembly 36 being fluidly connected in series between the discharge outlet 40 and the reservoir 32, other configurations are contemplated. For example, a schematic representation of a fluid pathway associated with an alternative embodiment implantable therapeutic substance delivery device 160 is shown in FIG. 6A. As with the delivery device 22 previously described, the delivery device 160 of FIG. 6A generally includes the reservoir 32, refill port assembly 34, access port assembly 36, flow restrictor mechanism 38, the metering mechanism 54, and the discharge outlet charge 40 that is otherwise fluidly coupleable to the catheter (not shown) where provided. However, the delivery device 160 of FIG. 6A provides first and second fluid pathways 162, 164 relative to the refill port assembly 34 and the access port assembly 36, respectively. In particular, the first fluid pathway 162 fluidly extends from the refill port assembly 34 to the reservoir 32, from the reservoir 32 to the metering mechanism 54, and then from the metering mechanism 54 to the discharge outlet 40. As shown by arrowheads in FIG. 6A, the first fluid pathway 162 is characterized by fluid flow occurring in only one direction.

The second fluid pathway 164 fluidly connects the access port assembly 36 with the flow restrictor mechanism 38; and the flow restrictor mechanism 38 with the discharge outlet 40. As shown by arrowheads in FIG. 6A, and commensurate with the description previously provided, fluid flow can occur in both directions along the flow pathway 164, to and from the access port assembly 36/flow restrictor mechanism 38 as well as to and from the flow restrictor mechanism 38/discharge outlet 40. During use, the delivery device 160 operates in a manner highly similar to that previously described with respect to the delivery device 22 (FIG. 4A). However, fluid (e.g., therapeutic substance) can flow directly from the pump/metering mechanism 54 to the discharge outlet 40 without interacting with the flow restrictor mechanism 38.

Figure 6B:
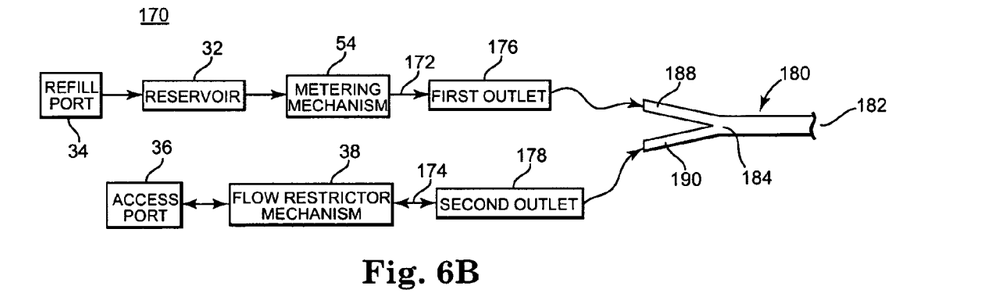

Yet another alternative embodiment implantable therapeutic substance delivery device 170 is illustrated in FIG. 6B. The delivery device 170 is similar in many respects to the delivery devices 22, 160 previously described, and again includes the reservoir 32, the refill port assembly 34, the access port assembly 36, the flow restrictor mechanism 38, and the metering mechanism 54. In addition, the delivery device 170 defines first and second fluid pathways 172, 174. As shown, the first fluid pathway 172 fluidly connects the metering mechanism 54 with a first discharge outlet 176, whereas the second fluid pathway 174 fluidly connects the flow restrictor mechanism 38 with a second discharge outlet 178. With this in mind, the system 170 includes a catheter 180 having a distal portion 182 (referenced generally) terminating at a distal outlet (not shown), as well as a proximal portion 186 forming first and second inlets 188, 190. With this configuration, the catheter 180 fluidly connects the inlets 188, 190 with the outlet 184. Further, each of the inlets 188, 190 are configured to be fluidly connected to a respective one of the discharge outlets 176, 178. With this configuration, then, the discharge outlets 176, 178 are effectively fluidly isolated from one another within the delivery device 170. Thus, during use, fluid flow (e.g., therapeutic substance) can readily flow from the metering mechanism 54 to the discharge outlet 176/catheter inlet 188 without passing through the flow restrictor mechanism 38.

Figure 6C:
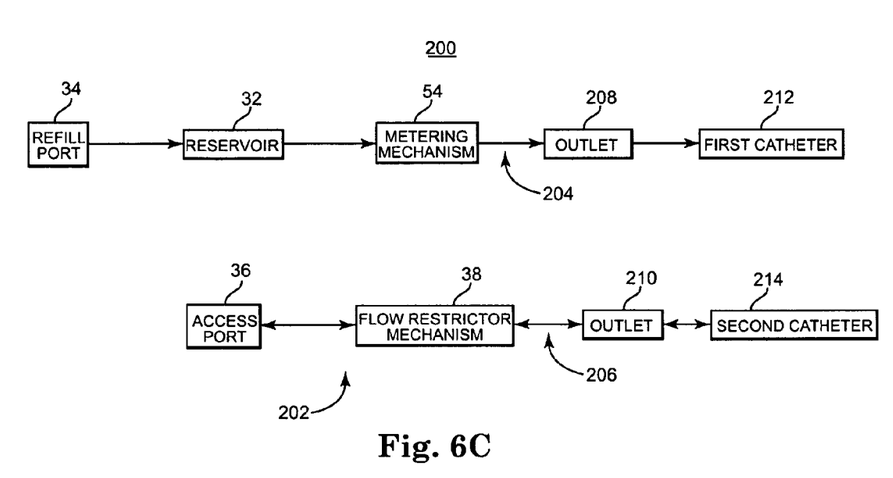

A related, alternative embodiment, implantable therapeutic substance delivery system 200 is provided in FIG. 6C. Once again, the system 200 includes a delivery device 202 including the reservoir 32, refill port assembly 34, access port assembly 36, flow restrictor mechanism 38, and metering mechanism 54. Further, the delivery device 202 defines first and second fluid pathways 204, 206 each terminating in a discharge outlet 208, 210, respectively. In addition, the system 200 includes first and second catheters 212, 214. As shown, the first catheter 212 is fluidly connected to the first fluid pathway 204 via the first discharge outlet 208. Conversely, the second catheter 214 is fluidly connected to the second fluid pathway 206 via the second discharge outlet 210. With this in mind, the system 200, and in particular the delivery device 202, functions in a manner highly similar to previous embodiments, with the metering mechanism 54 delivering therapeutic substance (not shown) from the reservoir 32 to the patient delivery site via the first catheter 212. Further, the access port assembly 36 is available for percutaneously injecting or withdrawing liquids via the second catheter 214, with fluid flow therebetween occurring across the flow restrictor mechanism 38 that otherwise functions as previously described. With the embodiment of FIG. 6C, an entirety of the first and second pathways 204, 206 are fluidly isolated from one another, via the provision of the two catheters 212, 214.

The implantable therapeutic substance delivery devices and related methods of use in accordance with principles of the present invention provide a marked improvement over previous designs. In particular, the flow restrictor mechanism affords a clinician the ability to readily confirm desired port assembly location while performing a liquid injection procedure. In addition, the flow restrictor mechanism does not prevent the clinician from performing other desired procedures normally performed through the access port assembly.

Although the present invention has been described with reference to preferred embodiments, workers skilled in the art will recognize that changes can be made in form and detail without departing from the spirit and scope of the present invention. For example, the flow restrictor mechanism has been described as being a spring-loaded check valve having a small central orifice formed therein. A wide variety of other configurations are also envisioned and fall within the scope of the present invention. For example, the flow restrictor mechanism can be an electronically-controlled valve assembly, a stop valve (e.g., globe, gate, butterfly, or ball valve), a plug valve, a needle valve, or other type of check valve (e.g., swing-type check valve, lift-type check valve, ball-type check valve, etc.). In more general terms, aspects of the present invention entail the provision of any flow restriction means positioned to effect fluid flow to and from the access port assembly relative to the discharge outlet, and is preferably adapted to have a set point feature that, depending upon the forces acting upon the flow restriction means, alters flow rate characteristics through the flow restriction means.

What is claimed is:

1. A human implantable liquid therapeutic substance delivery system comprising:
   a delivery device including:
      a housing defining a discharge outlet;
      a reservoir maintained by the housing for containing the therapeutic substance;
      an access port assembly fluidly connected to the discharge outlet via a fluid pathway, wherein the access port assembly includes an access port passage wall across which an access port septum is disposed;
      a refill port assembly apart from the access port assembly and fluidly connected to the reservoir, wherein the refill port assembly includes a refill port passage wall across which a refill port septum is disposed;
      wherein the access port septum and the refill port septum each provide a resealable barrier between an exterior of the housing and an interior of the housing; and
      a flow restrictor mechanism fluidly connected between the discharge outlet and the access port assembly, and fluidly connected between the discharge outlet and the refill port assembly, so as to establish, relative to the discharge outlet, an outflow fluid flow direction and an inflow fluid flow direction, the flow restriction mechanism configured to have flow restriction characteristics in the outflow direction that differ from flow restriction characteristics in the inflow direction.

2. The system of claim 1, wherein the reservoir includes a reservoir inlet fluidly connected to the refill port assembly and a reservoir outlet, and further wherein the reservoir outlet is fluidly connected to the fluid pathway.

3. The system of claim 2, wherein the delivery device further includes a metering mechanism fluidly connected to the reservoir outlet.

4. The system of claim 3, wherein the metering mechanism is fluidly connected to the discharge outlet.

5. The system of claim 4, wherein the flow restrictor mechanism is fluidly connected between the metering mechanism and the discharge outlet.

6. The system of claim 1, further comprising:
   an implantable catheter fluidly connected to the discharge outlet for delivering liquid introduced at the access port assembly such that the access port assembly is a catheter access port assembly.

7. The system of claim 1, wherein the flow restrictor mechanism is self-actuating.

8. The system of claim 1, wherein the flow restrictor mechanism is configured to provide a first effective orifice size in a first state, and a second effective orifice size in a second state, the first effective orifice size being less than the second effective orifice size, and further wherein the flow restrictor mechanism is biased to the first state.

9. The system of claim 8, wherein the flow restrictor mechanism is configured to maintain the first state in the presence of fluid flow in the outflow direction.

10. The system of claim 9, wherein the flow restrictor mechanism is configured to transition from the first state to the second state in the presence of fluid flow in the inflow direction.

11. The system of claim 9, wherein the flow restrictor mechanism is configured to transition from the first state to the second state in the presence of a vacuum formed in the access port assembly.

12. The system of claim 1, wherein the flow restrictor mechanism includes a valve plate having a thickness and defining a valve plate orifice through the thickness, a cylinder forming an inlet face having an inlet opening and outlet face having an outlet opening and slidably maintaining the valve plate between a first position in which the valve plate is fluidly sealed relative to the one of the inlet and outlet faces such that fluid flow through the flow restrictor mechanism is restricted to the valve plate orifice, and a second position in which the valve plate is not fluidly sealed relative to the outlet and inlet faces in which fluid flow through the flow restrictor mechanism is not restricted to the valve plate orifice, and a biasing device for biasing the valve plate to the first position.

13. The system of claim 12, wherein a diameter of the valve plate orifice is less than a diameter of the inlet opening or the outlet opening.

14. The system of claim 12, wherein the biasing device is a spring having a spring force selected to allow movement of the valve plate away from the outlet face when a pressure exerted upon the valve plate in the inflow direction exceeds a predetermined value.

15. A method of percutaneously performing a liquid substance exchange with an implantable therapeutic substance delivery device including a housing maintaining a reservoir for containing the therapeutic substance, a refill port assembly fluidly connected to the reservoir, and an access port assembly fluidly connected to a discharge port, the method comprising:
   providing a flow restrictor mechanism fluidly connected between the access port assembly and the discharge outlet, the flow restrictor mechanism including a valve plate having a thickness and defining a valve plate orifice through the thickness, and further wherein the flow restrictor mechanism is adapted to present a restriction to fluid flow from the access port assembly to the discharge port including a normal, maximum restriction state in which a restriction upon fluid flow through the flow restrictor is maximized, the flow restrictor configured to permit fluid flow through the valve plate orifice in the maximum restriction state;
   providing a liquid supply assembly including a needle fluidly connected to a supply of liquid, the needle terminating in a needle tip;

percutaneously delivering the needle tip through a septum associated with one of the refill port assembly and the access port assembly;

initiating injection of liquid through the needle;

determining whether the needle tip is disposed within the refill port assembly or the access port assembly based upon a sensed resistance to fluid flow through the needle tip while injecting the liquid through the needle; and determining whether to move the needle tip from the port assembly within which the needle tip is currently positioned based upon the sensed resistance to fluid flow.

16. The method of claim 15, wherein the method relates to refilling the reservoir with therapeutic substance.

17. The method of claim 15, wherein determining whether the needle tip is disposed within the refill port assembly is based upon a perceived flow rate from the needle tip.

18. The method of claim 15, further comprising:

providing a liquid withdrawal system including a withdrawal needle terminating in a tip;

percutaneously inserting the withdrawal needle tip into the access port assembly and beyond the access port assembly septum;

creating a vacuum in the access port assembly via the needle tip to cause the flow restrictor mechanism to transition from a first state to a second state; and withdrawing liquid from the patient, through the discharge opening and the access port assembly with the flow restrictor mechanism in the second state.

19. A human implantable therapeutic substance delivery system comprising:

a delivery device including:

a housing defining a discharge outlet;

a reservoir maintained by the housing for containing the therapeutic substance;

an access port assembly fluidly connected to the discharge outlet via a fluid pathway;

a refill port assembly apart from the access port assembly and fluidly connected to the reservoir; and flow restriction means for partially restricting a rate of fluid flow across the fluid pathway at least in a direction from the access port assembly to the discharge outlet, the flow restriction means adapted to permit fluid flow from the discharge outlet to the access port assembly, wherein in the flow restriction means includes a valve plate having a thickness and defines a valve plate orifice through the thickness, and further wherein the flow restriction means is transitionable from a normal, maximum restriction state in which a restriction upon fluid flow through the flow restriction means is maximized, the flow restriction means configured to permit fluid flow through the valve plate orifice in the maximum restriction state.

20. The system of claim 19, wherein the flow restriction means self-transitions from the maximum restriction state when subjected to fluid flow in a direction from the discharge outlet to the access port assembly.

21. The system of claim 19, wherein the flow restriction means is configured such that a maximum flow rate from the discharge outlet to the access port assembly is greater than a maximum flow rate from the access port assembly to the discharge outlet.

22. The system of claim 19, wherein the flow restriction means is adapted such that a maximum flow rate from the access port assembly to the discharge outlet is at least three times less than a maximum flow rate from the refill port assembly to the reservoir.

23. The system of claim 19, wherein the flow restriction means provides a fluid flow conduit having a diameter of approximately 0.005 inch in a flow direction from the access port assembly to the discharge outlet.

* * * * *